United States Patent [19]
Rubin

[11] Patent Number: 5,543,149
[45] Date of Patent: Aug. 6, 1996

[54] TREATMENT FOR INSECT BITES

[76] Inventor: Stan M. Rubin, 77 Fifth Ave., Troy, N.Y. 12180

[21] Appl. No.: 396,551

[22] Filed: Mar. 1, 1995

[51] Int. Cl.⁶ ........................................ A61K 9/06
[52] U.S. Cl. .................. 424/405; 424/409; 514/829; 514/830; 514/969
[58] Field of Search ................... 424/405, 94.2, 424/94.21, 409; 514/829, 830, 969

[56] References Cited

U.S. PATENT DOCUMENTS

| | | | |
|---|---|---|---|
| 2,917,433 | 12/1959 | Goldman | 167/65 |
| 3,324,002 | 6/1967 | Antonides | 167/73 |
| 3,409,719 | 11/1968 | Noe et al. | 424/94 |
| 3,860,702 | 1/1975 | Buell | 424/94 |
| 4,678,668 | 7/1987 | Darras | 424/94.1 |
| 5,006,562 | 4/1991 | Steltenkamp | 514/625 |

FOREIGN PATENT DOCUMENTS

84/02846  8/1984  WIPO.

OTHER PUBLICATIONS

Bilton, *Chemical Abstracts*, vol. 101, 1984, #157708p.
Hägermark "Influence of Antihistamines, Sedatives, and Aspirin on Experimental Itch" *Acta Dermatovener* 53, 363–368 (1973).
Agostinucci et al. "Effect of Papain on Bee Venom Toxicity" *Toxicon* 19, 851–855 (1981).
Rodeheaver et al. "Proteolytic Enzymes as Adjuncts to Antimicrobial Prophylaxis . . ." *Amn. J. Surgery* 129, 537–544 (1975).
Morgan "Topical Therapy of Pressure Ulcers" *Surgery, Gynecology & Obstetrics* 141, 945–947 (1975).

Primary Examiner—Thurman K. Page
Assistant Examiner—P. Webber
Attorney, Agent, or Firm—Heslin & Rothenberg, P.C.

[57] ABSTRACT

A method and compositions for reducing the itch associated with the bite of a blood-feeding insect such as a mosquito or black fly are disclosed. The method entails applying a topical pharmaceutical formulation of papain, pancreatin or subtilisin, optionally including urea, to the skin proximate to the bite. Compositions are provided in the form of solutions, lotions, ointments and salves containing papain, pancreatin or subtilisin and, optionally, urea.

11 Claims, No Drawings

TREATMENT FOR INSECT BITES

FIELD OF THE INVENTION

The invention relates to a method for reducing the itch associated with the bite of a blood feeding insect such as a mosquito or black fly. The method entails applying a topical pharmaceutical formulation of papain, pancreatin or subtilisin to the skin proximate to the bite.

BACKGROUND OF THE INVENTION

Adult black flies, notably *Simulium venustum* and *Prosimulium hirtipes*, and mosquitoes of the Aedes, Anopheles and Culex genera are well known for their blood feeding habit. The feeding behavior involves puncturing the skin of the host, injecting a small quantity of anticoagulant, and ingesting blood. The reaction of the human host to the injection of the anticoagulant gives rise to swelling, redness and itching in the area immediately surrounding the bite.

SUMMARY OF THE INVENTION

The present invention is directed to a method and compositions for reducing the itching associated with black fly and mosquito bites. The method comprises applying a therapeutically effective amount of papain, pancreatin or subtilisin in a suitable pharmaceutical carrier to the surface of the skin proximate to the bite. The pharmaceutical carrier may be water based or primarily lipid and preferably contains, in addition, urea.

In another aspect the invention relates to pharmaceutical compositions for treating mosquito and black fly bites. The compositions comprise a therapeutically effective amount of the foregoing enzymes and a pharmaceutical carrier adapted for topical application. The carrier may be a solution, a lotion, an ointment or a salve.

DETAILED DESCRIPTION OF THE INVENTION

Over the years, there have been anecdotal reports of the utility of papain, commonly in the form of meat tenderizer, for the first aid treatment of hymenoptera stings. It has been suggested that a paste of the material can be applied topically and rubbed into the site of the sting, resulting in lessened swelling. However, the efficacy of papain in reducing bee venom toxicity, suggested in the anecdotal reports, has not been confirmed in the only controlled study known to the inventor. Thus, Agostinucci et al. [*Toxicon* 19, 851–855 (1981)] examined the effect of papain paste topically applied after an intradermal injection of bee venom in mice and concluded that "the results, however, do not substantiate the theory. No marked inhibition of lesion development could be shown in any of the animals receiving papain or Adolph's Meat Tenderizer™ by intradermal injection or topical application."

Given the inefficacy of papain in the treatment of stings by venomous insects, it is particularly surprising to discover that papain, pancreatin and subtilisin are effective in reducing the itch associated with the bites of blood feeding insects. Although applicant does not wish to be limited by the hypothesis, it is possible that the efficacy in one case and not in the other arises from a distinction in the etiology of the two reactions. In the case of stinging insects, a highly specialized mixture of irritants and lytic agents is injected from a specially evolved gland; the venom is particularly adapted to cause tissue destruction, pain and/or paralysis. On the other hand, the material injected by biting insects (mosquitoes and black flies) is essentially saliva modified to inhibit blood coagulation. In any event, applicant has found that the topical application of papain, pancreatin or subtilisin is effective in reducing the itch associated with mosquito and black fly bites.

The active ingredients in the methods and compositions of the invention are papain (Chemical Abstracts Registry No. 9001-73-4), subtilisin (Chemical Abstracts Registry No. 9014-01-1) and pancreatin (Chemical Abstracts Registry No. 8049-47- 6); all are commercially available.

The topical pharmaceutical carrier may include any substance capable of dispersing and maintaining contact between the active ingredients and the skin. The vehicle may be glycerin, alcohol or water based. Examples of such vehicles include aloe vera which is a gel base, together with ethanol, isopropyl alcohol, water, propylene glycol and a non-ionic surfactant such as laureth-4. Other water-based alcohol/glycerin vehicles and carriers are within the scope of the present invention. A typical water-based lotion will contain from 45 to 50 parts of glycerin, one to three parts Tween 80™, from 45 to 50 parts of water and from 1 to 50 papain, pancreatin or subtilisin.

Also included in the scope of the invention are ointments, emulsions or dispersions in which water, if present, is a minor constituent. Typical ointment formulation comprises from 90 to 98 parts of a mixture of petrolatum, mineral oil, mineral wax and wool wax alcohol, from 0.5 to 3 parts of a mixture of polyoxyethylene and sorbitan monooleate (Tween 80™), from 1 to 5 parts of water, and from 1 to 50 parts papain, pancreatin or subtilisin. Another suitable non-aqueous ointment can be prepared from 95 parts of liquid petrolatum usp, 5 parts polyethylene and from 1 to 50 parts of the appropriate enzyme. The resulting ointment spreads easily and has an even consistency over wide temperature extremes. It is, in addition, non-irritating and non-sensitizing.

Formulations of the enzymes of interest may also be prepared containing from 0 to 25% by weight of urea. In general, in such urea containing ointments, the water content will vary from 5 to 50% by weight of the composition. Any suitable ointment carrier may be used such as lanolin, ethylene glycol polymers and the like. In the case of formulations containing urea, it is known in the art that borate salts may often be added to stabilize the pharmaceutical composition (see U.S. Pat. No. 2,917,433, the disclosure of which is incorporated herein by reference).

Water based compositions may also be employed, in which case the enzyme will commonly be in solution and the aqueous solution may, if desired, be thickened with a suitable gel to provide a less mobile composition. Such compositions are well known in the art. In the water based compositions, the enzyme will once again be present in an amount from 1 to 50% by weight.

To demonstrate the efficacy of the compositions of the invention, a subtilisin paste was prepared by crushing Bausch and Lomb Renu™ enzymatic cleaning tablets, which are believed to contain 25 to 60 mg of a 3:1:1 mixture of sodim bicarbonate, citric acid and sodium chloride and 25–30 mg subtilisin, in as little water as possible to make a paste. Paste was applied to mosquito bites in which the wheal had developed to approximately 2 to 3 cm in diameter. Within 20 minutes of application, itching associated with the insect bite was substantially completely relieved. The onset of the effect was sudden, and appeared within 20 minutes in all instances. When multiple bites received at substantially the same time were treated at different intervals, the itching in each bite subsided within 20 minutes of treatment of that particular bite. Similar tests were carried out with papain and pancreatin pastes using Allergan Enzymatic Cleaner tablets believed to consist of 8 parts by weight papain, 8 parts by weight cysteine hydrochloride, 1.6 parts $KH_2PO_4$, 16 parts $NaHCO_3$, 6.4 parts $Na_2EDTA$, 58.4 parts NaCl and 1.6 parts PEG-4000, and with Alcon Opti-zyme™ tablets containing a similar formulation of pancreatin.

While the invention has been particularly shown and described with reference to preferred embodiments thereof, it will be understood by those skilled in the art that other changes in form and details may be made therein without departing from the spirit and scope of the invention. In particular, it will be obvious to those of skill in the art that combinations of the foregoing enzymes will function in a similar manner to the individual enzymes.

I claim:

1. A method for reducing the itch associated with black fly and mosquito bites comprising applying an itch-reducing amount of an enzyme chosen from the group consisting of papain, pancreatin and subtilisin in a pharmaceutical carrier to the surface of a patient's skin proximate to said mosquito or black fly bite.

2. A method according to claim 1 wherein said enzyme is papain.

3. A method according to claim 1 wherein said enzyme is pancreatin.

4. A method according to claim 1 wherein said enzyme is subtilisin.

5. A method according to claim 1 wherein said enzyme is applied as a solution in an aqueous pharmaceutical carrier.

6. A method according to claim 5 wherein said pharmaceutical carrier further comprises urea.

7. A method according to claim 1 wherein said enzyme is applied as an emulsion or dispersion in a lipid-containing pharmaceutical carrier.

8. A method according to claim 7 wherein said pharmaceutical carrier further comprises urea.

9. A pharmaceutical composition for treating mosquito and black fly bites comprising an itch-reducing amount of subtilisin and urea in a pharmaceutical carrier adapted for topical application.

10. A pharmaceutical composition in the form of an ointment or salve, according to claim 9.

11. A pharmaceutical composition in the form of a lotion or solution, according to claim 9.

* * * * *